US006685931B1

(12) United States Patent
Grint et al.

(10) Patent No.: US 6,685,931 B1
(45) Date of Patent: Feb. 3, 2004

(54) TREATMENT OF HEPATITIS C VIRUS INFECTIONS WITH INTERLEUKIN-10

(75) Inventors: Paul C. Grint, San Diego, CA (US); David R. Nelson, Gainesville, FL (US); Gary L. Davis, Gainesville, FL (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/467,425

(22) Filed: Dec. 20, 1999

Related U.S. Application Data

(63) Continuation-in-part of application No. 09/425,716, filed on Oct. 22, 1999, now abandoned, which is a continuation-in-part of application No. 09/293,742, filed on Apr. 16, 1999, now abandoned, which is a continuation-in-part of application No. 09/218,842, filed on Dec. 22, 1998, now abandoned.

(51) Int. Cl.[7] ........................ A61K 38/20; A61K 38/21; A61K 38/00; A01N 25/00

(52) U.S. Cl. .................. 424/85.2; 424/85.7; 424/149.1; 424/189.1; 514/2; 514/8; 514/12; 514/893; 514/894

(58) Field of Search .............................. 424/85.2, 85.4, 424/149.1, 189.1, 85.7; 435/91.31; 514/2, 8, 12, 885, 893, 894

(56) References Cited

U.S. PATENT DOCUMENTS

| | | | | |
|---|---|---|---|---|
| 5,762,923 A | * | 6/1998 | Gross et al. | 424/85.7 |
| 6,159,937 A | * | 12/2000 | Larsen et al. | 514/15 |

FOREIGN PATENT DOCUMENTS

| | | |
|---|---|---|
| WO | WO 95 19780 | 7/1995 |
| WO | WO 97 16204 | 5/1997 |
| WO | WO 97 26278 | 7/1997 |
| WO | WO 97 40849 | 11/1997 |

OTHER PUBLICATIONS

J Hepatology. 1995, 23(Suppl,2):32–36. Main J. Future studies of combination therapy for chronic hepatitis C: optimizing response rates for each hepatitis C population.*

J hepatology. 1995, 23(Suppl. 2):22–25. Bizollon T et al. New Approaches to the treatment of hepatitis C virus infection after livr transplant using ribavirin.*

Hepatology, 1997, 25(6): 1382–1389. Louis H et al. Production and role of Interleukin–10 in concanavalin A–induced hepatitis in Mice.*

Digestive diseases and Sciences. vol. 41, No. 12 Dec. 9, 1996 Suppl). pp. 126S–130S. Marcellin P et al. Interferon–alpha therapy for chronic hepatitis C in special patient populations.*

Martin. J et al. Effects of the ribavirin–interferon alpha combination on the cultured peripheral blood mononuclear cells from chronic hepatitis C patients (1998), Cytokine, vol. 10, No. 8 pp. 635–644.*

Louis. H et al. Production and Role of Interleukin–10 in Concanavalin A–induced Hepatitis in Mice (1997), Hepatology, vol. 25, pp. 1382–1389.*

Gerber. M, Pathology of hepatitis C. (1994), FEMS Microbilogy Reviews vol. 14, pp. 205–210.*

Nelson, D.R., et al, *Activation of Tumor Necrosis Factor*, Digestive Diseases and Sciences, vol. 42, No. 12, Dec., 1997, pp. 2487–2494.

Nelson, David R., et al, *A Pilot Study Recombinant Human Interleukin 10*, Hepatology, vol. 30, No. 4, Part 2, Oct. 1999, p. 189A, Abstract 115.

McHutchison, J.G.,*A Pilot study of daily subcutaneous interleukin–10*, Journal of Interferon and Cytokine Research, vol. 19, No. 11, Nov., 1999, pp. 1265–1270.

* cited by examiner

*Primary Examiner*—Lorraine Spector
*Assistant Examiner*—Jegatheesan Seharaseyon
(74) *Attorney, Agent, or Firm*—Thomas D. Hoffman

(57) ABSTRACT

The hepatoprotective effect of IL-10 is described, in particular, the use of interleukin-10 in the treatment of liver damage (e.g. fibrosis or cirrhosis) in a difficult-to-treat patient afflicted with chronic hepatitis C virus infection who has failed to respond to, or achieve a sustained virologic response to an anti-HCV therapy(e.g., interferon-$\alpha$ in combination with ribavirin).

12 Claims, No Drawings

TREATMENT OF HEPATITIS C VIRUS INFECTIONS WITH INTERLEUKIN-10

CROSS-REFERENCE TO RELATED APPLICATIONS

This application is a continuation-in-part of U.S. Ser. No. 09/425,716, filed Oct. 22, 1999, now abandoned which is a continuation-in-part of U.S. Ser. No. 09/293,742, filed Apr. 16, 1999, now abandoned which is a continuation-in-part of U.S. Ser. No. 09/218,842, filed Dec. 22, 1998 now abandoned.

BACKGROUND OF THE INVENTION

The invention is directed to the use of interleukin-10 to improve liver histology in patients afflicted with chronic hepatitis C virus infections. In particular, the invention relates to the use of interleukin-10 to reduce hepatic fibrosis in difficult-to-treat patients afflicted with chronic hepatitis C virus infections.

Chronic hepatitis C is an insidious and slowly progressive disease having a significant impact on morbidity and mortality. While many patients who contract hepatitis C will have subclinical or mild disease, HCV infection causes progressive liver damage in the majority of those infected. At least 80% of the individuals who contract HCV will develop chronic infection and hepatitis, a disease state characterized by fluctuating serum transaminase abnormalities and inflammatory with or without fibrosis lesions on liver biopsy. Twenty to fifty percent of these will eventually progress to cirrhosis and 1–2% will develop liver cancer after a 10–20 year period.

Multiple factors influence the hepatitis C virus-host interaction resulting in a unique individual disease pattern. In individuals chronically infected with HCV, there is persistent viremia and liver damage despite the presence of both humoral and cellular responses. The mechanisms responsible for hepatocellular injury are not fully understood. The role of IL-10 in inhibiting liver fibrogenesis has been evaluated in the mouse. Two studies (Louis et al., Heptatology, 1998;28:1607–1615; and Thompson et al., Heptatology, 1998;28:1597–1606) showed that IL-10 knock-out mice develop significantly more severe fibrosis than wild-type mice.

At the present time, the interferon-α-2b/ribavirin combination therapy is the best available treatment option. Sustained virologic response to IFNα-ribavirin combination therapy occurs in about 40–45% of those treated. For those patients who fail interferon-α-2b/ribavirin combination therapy, there is currently no alternative to prevent the progression of liver disease. Thus, a need exists for alternative therapies for the treatment of chronic HCV infection.

SUMMARY OF THE INVENTION

The present invention fulfills this need by providing materials and methods for treating hepatitis C virus infection and liver damage in difficult-to-treat patients.

One aspect of the invention provides a method for improving liver histology in a difficult-to-treat patient afflicted with a chronic hepatitis C virus infection comprising administering an effective amount of an interleukin-10 to such a patient.

Another aspect of the invention provides a method of treating or preventing hepatitis C virus infection in a difficult-to-treat patient afflicted with a chronic hepatitis C virus infection comprising administering an effective amount of an interleukin-10 in association with an effective amount of an an effective amount of an interferon-α to a patient in need of such treating or preventing Yet another aspect of the invention provides a method of decreasing or preventing liver damage (e.g. fibrosis or cirrhosis) caused by hepatitis C virus in a difficult-to-treat patient afflicted with a chronic hepatitis C virus infection comprising administering an effective amount of interleukin-10 to such a patient to decrease or prevent liver damage (e.g. fibrosis or cirrhosis) caused by the hepatitis C virus.

Still another aspect of the invention provides a method for treating and/or preventing hepatic fibrosis in a difficult-to-treat patient afflicted with a chronic hepatitis C virus infection comprising administering an effective amount of an interleukin-10 to such a patient.

In preferred embodiments of the present invention, there are provided pharmaceutical compositions for treating hepatitis C virus infection in a mammal comprising an effective amount of interleukin-10 and a pharmaceutically acceptable carrier. Optionally, the pharmaceutical composition of the invention may contain at least one other any-viral agent, such as, for example interferon-α and/or ribavirin. In another preferred embodiment of the present invention, the interferon-α is recombinant interferon-α-2b or pegylated interferon-α-2b and the interleukin-10 is recombinant human interleukin-10.

DETAILED DESCRIPTION OF THE INVENTION

The phrase "a difficult-to-treat patient afflicted with chronic hepatitis C virus infection" as used herein means a patient afflicted with chronic hepatitis C virus("HCV") infection who has failed to achieve a sustained virologic response after treatment with any type of anti-HCV therapy including, but not limited to, interferon-α, or pegylated interferon-α, alone or in combination with ribavirin, or a non-responder patient to any such anti-HCV therapy as well as a treatment naive patient afflicted with chronic HCV infection with HCV genotype 1A or 1B or a treatment naive patient infected with multiple HCV genotypes including type 1. who has never taken any anti-HCV therapy.

The term "treatment naive patients" afflicted with chronic HCV infection as used herein means patients with HCV who have never been treated with ribavirin or any interferon, including, but not limited to, interferon-α or pegylated interferon-α, alone or in combination with ribavirin.

The term "sustained virologic response" as used herein in reference to difficult-to-treat patients afflicted with chronic HCV infection means there is no detectable HCV-RNA in the serum of patients treated with interferon-α, pegylated interferon-α alone or in combination with ribavirin for at least 24–48 weeks after the end of the combined therapy treatment.

The term "no detectable HCV-RNA" as used herein means that there are fewer than 100 copies/mL of HCV-RNA in the serum as measured by quantative PCR("qPCR") testing.

The term "liver histology" as used herein means the minute structure, composition and function of the liver as determined by examination of liver biopsy samples for inter alia, portal inflamrnmation, piecemeal or bridging necrosis, lobular injury, cirrohosis and fibrosis. Evaluation of the biopsies may be performed by a pathologist using the Knodell Histology Activity Score, or the modified Knodell Score (Ishak et al.,J. Hepatol, 1995;22:696–699), or the Metavir scoring system (Bedossa et al., Hepatology, 1996;24:289–293). Efficacy of study treatments was assessed by comparing the liver histology, especially the degree of fibrosis and/or inflammatory activity observed at Baseline with that present at the end of treatment in accordance with the present invention.

Elevated serum alanine aminotransferase (ALT) and aspartate aminotransferase (AST) are known to occur in uncontrolled hepatitis C. A complete response to treatment is generally defined as the normalization of these serum enzymes, particularly ALT (Davis et al., 1989, *New Eng. J. Med.* 321:1501–1506). Interleukin-10 (IL-10) has now been surprisingly found to be effective in normalizing ALT and in reducing hepatic fibrosis.

IL-10 administered as monotherapy in accordance with the present invention has been found not only to reduce hepatic fibrosis, but also to suppress host-mediated immunopathology, a component contributing to the chronic liver damage associated with HCV infection., even though IL-10 monotherapy does not lower or eradicate serum HCV-RNA levels Thus, IL-10 can be used in accordance with the present invention to improve liver function and to modulate the inflammatory response and the fibrosis process responsible for much of the destruction of the liver of difficult-to-treat patients afflicted with chronic HCV infection.

IL-10, as defined herein, include proteins which have an amino acid sequence substantially identical to a known sequence of a mature (i.e., lacking a secretory leader sequence) IL-10 disclosed in U.S. Pat. No. 5,231,012, and has biological activity that is common to native IL-10. For the purposes of this invention, both glycosylated (e.g., produced in eukaryotic cells such as yeast or CHO cells) and unglycosylated (e.g., chemically synthesized or produced in *E. coli*) IL-10 are equivalent and can be used interchangeably. Also included are muteins and other analogs, including viral IL-10, which retain the biological activity of IL-10.

As used herein, IL-10 can mean the intact protein or substitutions, additions, or deletions which do not substantially diminish the replication inhibiting and/or immunomodulating activity of IL-10. Thus, the BCRF1 gene product can be included in this definition. Although human, mouse and viral IL-10 may be used in the practice of the invention, the use of recombinant human IL- 10 is most preferred.

IL-10 suitable for use in the invention can be obtained from a number of sources. IL-10 can be isolated from culture media of activated T-cells capable of secreting the protein. Additionally, the IL-10 or active fragments thereof can be chemically synthesized using standard techniques known in the art. See, e.g., Merrifield, 1986, *Science* 233:341–347 and Atherton et al., *Solid Phase Peptide Synthesis, A Practical Approach*, 1989, IRL Press, Oxford.

Preferably, the protein or polypeptide is obtained by recombinant techniques using isolated nucleic acids encoding the IL-10 polypeptide. General methods of molecular biology are described, e.g., by Sambrook et al., 1989, *Molecular Cloning, A Laboratory Manual*, 2d Ed., Cold Spring Harbor, N.Y. and Ausubel et al. (eds). *Current Protocols in Molecular Biology*, Green/Wiley, New York (1987 and periodic supplements). The appropriate sequences can be obtained using standard techniques from either genomic or cDNA libraries. DNA constructs encoding IL-10 may also be prepared synthetically by established standard methods, e.g., in an automatic DNA synthesizer, and then purified, annealed, ligated and cloned in suitable vectors. Atherton et al., Solid Phase Peptide Synthesis, A Practical Approach, 1989, IRL Press, Oxford. Polymerase chain reaction (PCR) techniques can be used. See e.g., PCR Protocols: A Guide to Methods and Applications, 1990, Innis et al. (ed.), Academic Press, N.Y.

The DNA constructs may contain the entire native sequence of IL-10 or a homologue thereof. The term "homologue" is intended to indicate a natural variant of the DNA sequence encoding IL-10 or a variant or fragment produced by modification of the DNA sequence. Examples of suitable modifications of the DNA sequence are nucleotide substitutions which do not give rise to another amino acid sequence and nucleotide substitutions which do give rise to a different amino acid sequence and therefore, possibly, a different protein structure. Other examples of possible modifications are insertions of one or several nucleotides into the sequence, addition of one or several nucleotides at either end of the sequence, or deletion of one or several nucleotides at either end or within the sequence. Any homologous DNA sequence encoding a protein which exhibits IL-10 activity similar to that of the naive protein is contemplated for use in the claimed invention.

The nucleotide sequences used to transfect the host cells can be modified, as described above, to yield IL-10 muteins and fragments with a variety of desired properties. Such modified IL-10 can vary from the naturally-occurring sequence at the primary level, e.g., by amino acid insertions, substitutions, deletions and fusions. Preferably, amino acid substitutions will be conservative; i.e., basic amino acid residues will be replaced with other basic amino acid residues, etc. These modifications can be used in a number of combinations to produce the final modified protein chain.

Amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translltional variants, e.g., glycosylation variants or proteins which are conjugated to polyethylene glycol (PEG), etc. Such variants can be used in this invention as long as they retain the biological activity of IL-10.

Fragments of IL-10 can be generated, for example, by mechanical or chemical disruption of the complete protein. Modifications to IL-10 can be obtained by cloning modified nucleic acids encoding the polypeptide in an expression system capable of producing the modified protein or fragments thereof (see generally Sambrook, et al., *Molecular Cloning: A Laboratory Manual*, 2nd Ed., 1989, Cold Spring Harbor, N.Y.). Modified nucleic acids encoding IL-10 can be made, for example, by site directed mutagenesis, by making synthetic genes having the modification, or by making nucleic acid fuisions. A fuision can be used, for example, to increase the solubility of the protein. The activity of such a modified IL-10 or fragments can be determined utilizing the methods taught in U.S. Pat. No. 5,231,012.

Preferably, human IL-10 is used for the treatment of humans, although viral or mouse IL-10, or IL-10 from some other mammalian species, could be used instead. Most preferably, the IL-10 used is recombinant human IL-10. Recombinant human IL-10 can be obtained from the unpurified or purified supernatants of recombinant human IL-10 cDNA-transfected COS-7 cells as previously described by Hsu et al. (*Science*, (1990) 250:745). Recombinant production of mouse and human IL-10 is also described in U.S. Pat. No. 5,231,012. The cloning and expression of viral IL-10

(BCRF1 protein) from Epstein Barr virus is disclosed by Moore et al. (*Science* 248:1230, 1990) and in U.S. Pat. No. 5,627,155. Recombinant human IL-10 is available from Schering-Plough Corporation, Kenilworth, N.J.

The methods of the invention involve administration of IL-10 to a human subject. The compounds can be administered by means well known to those of skill in the art for administration of proteins. Such means, and the proper dosages, are exemplified by the administration of such proteins as insulin, interleukin-2 and immunoglobulins, for example, as are known to those of skill in the art. Parenteral and sublingual administration are typically preferred. In addition, the IL-10 can be administered to blood cells removed from the body of the subject and returned after treatment.

The exact amount of IL-10 required will vary from subject to subject, depending on the species, age, weight and general condition of the subject, the severity of the disease that is being treated, the particular IL-10 used, its mode of administration, the side effects encountered, and the like.

Generally, when administered to cells the amount of IL-10 administered is between about 0.001 and 1 units/ml, preferably between about 0.01 and 0.1 units/ml. When administered directly to a patient, the amount of IL-10 administered is between about 1,000 and 1,000,000 units, preferably between about 20,000 and 200,000 units. The appropriate amount can be maximized using standard procedures. The units used here are defined as the amount that will produce half maximal stimulation of the MC9 mast cell line (Thompson-Snipes et al., 1991*, J. Exp. Med.* 173:507). An MC/9 line is deposited with American Type Culture Collection under Accession No. CRL-8306.

The IL-10 will preferably be in unit dosage form suitable for single administration of a precise dosage and may include an effective amount of the selected compound in combination with a pharmaceutically acceptable carrier, for example, saline. By the term "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. Actual methods of preparing such dosage forms are known, or will be apparent, to those skilled in this art; for example, see Remington's Pharmaceutical Sciences (Martin, E. W., ed., Mack Publishing Company, Easton, Pa.).

Administration of IL-10 is preferably parenteral by intraperitoneal intravenous, subcutaneous or intramuscular injection or infusion or by an other acceptable systemic method. Injectables can be prepared in conventional forms, either as liquid solutions or suspensions, solid forms suitable for solution or suspension in liquid prior to injection, or as emulsions. Administration by intramuscular or subcutaneous injection is most preferred. Alternatively, the IL-10 may be administered by an inplantable or injectable drug delivery system. See, e.g., Urquhart et al, 1984*, Ann. Rev. Pharmacol. Toxicol.* 24:199; Lewis, ed., 1981*, Controlled Release of Pesticides and Pharmaceuticals*, Plenum Press, New York, N.Y.; and U.S. Pat. Nos. 3,773,919, and 3,270,960. Another approach for parenteral administration involves use of a slow release or sustained release system, such that a constant level of dosage is maintained. See, e.g., U.S. Pat. No. 3,710,795. Continuous subcutaneous administration can also be accomplished by, for example, a pulsatile electronic syringe driver (Provider Model PA 3000, Pancretec Inc., San Diego Calif.), a portable syringe pump such as the Graseby model MS 16A (Graseby Medical Ltd., Watford, Herts England), or a constant infusion pump such as the Disetronic Model Panomat C-5. Osmotic pumps, such as that available from Alza, may also be used. Since use of continuous subcutaneous injections allows the patient to be ambulatory, it is preferred over use of continuous intravenous injections. Oral administration may also be carried out, using well known formulations which protect the IL-10 from gastrointestinal proteases.

Compositions useful for administration of such drugs are well known. See, e.g., Remington's Pharmaceutical Science, 11th Ed., 1990, Mack Publishing Co., Easton, Pa. When administered parenterally, the IL-10 is typically formulated in a unit dosage injectable form (solution, suspension, emulsion) in association with a pharmaceutical carrier. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other source proteins at a concentration in the range of about 5 to 20 mg/ml. Any of the well known carrier proteins such as human serum albumin can also be added if desired.

IL-10 can also be delivered by standard gene therapy techniques, including e.g., direct DNA injection into tissues, the use of recombinant viral vectors, or phospholipid and implantation of transfected cells. See, e.g., Rosenberg, 1992*, J Clin. Oncol.* 10:180. Or WO 98/35554 (published Aug. 20, 1998).

IL-10 is administered to a difficult-to treat human patient in an amount effective to improve liver histology, e.g. to reduce liver fibrosis, and inflammation, and/or to provide an anti-viral and/or hepatoprotective effect. As used herein the term "effective amount" means an amount sufficient to reduce or eliminate viral load, e.g., inhibit HCV replication (when used in association with an anti-viral agent such as interferon-α), and/or to prevent or ameliorate liver damage, e.g., inflammation and/or fibrosis, and/or to strabilize or lower ALT levels The effective amount for a particular patient may vary depending on such factors as the age of the patient, the route of administration, the severity disease, and the like. The effective dose of IL-10 typically will range from about 0.05 to about 25 μg/kg/day, preferably from about 0.1 to about 20 μg/kg/day, more preferably from about 1 to about 10 μg/kg/day, or is in the range of about 1 to about 8 μg/kg, daily or three times a week (TIW). or more preferably about 4 μg/kg or 8 μg/kg daily or TIW.

Generally, treatment is initiated with smaller dosages which are less than the optimum dose of the compound. Thereafter, the dosage is increased by small increments until the optimum effect under the circumstance is reached. Determination of the proper dosage and administration regime for a particular situation is within the skill of the art.

Frequency of injection of the IL-10 composition will depend on the form of the composition. It will be understood that injection will be less frequent (e.g., once or twice a week) when using sustained release formulations or long-acting polymer conjugates. A single injection may be sufficient when using viral vectors to express the cytokine in vivo.

Duration of treatment is at least about one month, more preferably at least about 3 months, and most preferably at least about 12 months. A proper course of treatment (dose, duration, etc.) will depend on a number of factors including, but not limited to, the age and weight of the patient and the pathology of disease, e.g., viral load, severity of liver damage. The determination of an appropriate treatment regime is well within the skill of the art.

A person suffering from chronic hepatitis C infection usually exhibits one or more of the following signs or symptoms: (a) elevated ALT, (b) positive test for anti-HCV antibodies, (c) presence of HCV as demonstrated by a positive test for HCV-RNA, (d) clinical stigmata of chronic liver disease, (e) hepatocellular damage. Such criteria may not only be used to diagnose hepatitis C, but can be used to follow and evaluate a patient's response to drug treatment. Such parameters may also be used to modulate the dose and duration of treatment.

IL-10 may be used alone, or in conjunction, combination, or concurrent with, one or more other anti-viral drugs, including, but not limited to lamivudine, zidovudine, ribavirin and/or interferon-α(IFN-α), such as interferon alpha-2a, interferon alpha-2b or pegylated interferon-α., i.e., pegylated interferon alpha-2a or pegylated interferon alpha-2b.

In the practice of the invention, the terms "combined/concurrent administration", in association with", and "in conjunction with" are used synonymously and mean that the drugs, e.g., IL-10, lamivudine, zidovudine, ribavirin,and interferon-α, are administered to the subject either (a) simultaneously in time (optionally by formulating the two together in a common carrier), or (b) at different times during the course of a common treatment schedule. In the latter case, the two compounds are administered sufficiently close in time to achieve the intended effect. Typically, if one agent is administered within about the half-life of the first agent, the two agents are considered to be concurrently administered. The active agents, i.e., IL-10, interferon-α and ribavirin, may be administered ribavirin together in a single pharmaceutical composition or separately. The active agents,e.g., IL-10, interferon-α and optionally ribavirin,) should be present in the patient at sufficient combined levels to be therapeutically effective. The routes of administration and the duration of administration of the IL- 10, interferon-α and ribavirin may be the same or different.

The term "interferon-α" as used herein means the family of highly homologous species-specific proteins that inhibit viral replication and cellular proliferation and modulate immune response. Typical suitable interferons-αinclude, but are not limited to, recombinant interferon alfa-2b such as Intron®-A interferon available from Schering Corporation, Kenilworth, N.J., recombinant interferon alfa-2a such as Roferon® A interferon available from Hoffmann-La Roche, Nutley, N.J., recombinant interferon alpha-2c such as Berofor® alpha 2 interferon available from Boehringer Ingelheim Pharmaceutical, Inc., Ridgefield, Conn., interferon alpha-n1, a purified blend of natural alfa interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alfa-n3 a mixture of natural alfa interferons made by Interferon Sciences and available from the Purdue Frederick Co., Norwalk, Conn., under the Alferon Tradename. The use of interferon alfa-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

The term "pegylated interferon-α" as used herein means polyethylene glycol modified conjugates of α-interferon, preferably interferon alfa-2a and -2b. The preferred polyethylene-glycol-interferon alfa -2b conjugate is $PEG_{12000}$-interferon alfa 2b which is available from Schering-Plough Research Institute, Kenilworth, N.J. The phrases "12,000 molecular weight polyethylene glycol conjugated interferon alpha","$PEG_{12000}$-IFN alfa-2b conjugate", and "$PEG_{12000}$-IFN alfa" as used herein mean conjugates such as are prepared according to the methods of International Application No. WO 95/13090 and containing urethane linkages between the interferon-alfa-2a or -2b amino groups and polyethylene glycol having an average molecular weight of 12000.

The preferred $PEG_{12000}$-interferon -alfa-2b is prepared by attaching a PEG polymer to the epsilon amino group of a lysine residue in the interferon alfa-2b molecule. A single $PEG_{12000}$ molecule is conjugated to free amino groups on an IFN alfa-2b molecule via a urethane linkage. This conjugate is characterized by the molecular weight of $PEG_{12000}$ attached. The $PEG_{12000}$-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

Other interferon-α conjugates can be prepared by coupling an interferon alfa to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. No. 4,766,106, U.S. Pat. No. 4,917,888, European Patent Application No. 0 236 987, European Patent Application Nos. 0510 356, 0 593 868 and 0 809 996 (pegylated interferon alfa-2a) and International Publication No. WO 95/13090.

In the practice of the invention, the terms "combined/concurrent administration" and "in conjunction with" are used synonymously and mean that the drugs, e.g., IL-10 and interferon-α, are administered to the subject either (a) simultaneously in time (optionally by formulating the two together in a common carrier), or (b) at different times during the course of a common treatment schedule. In the latter case, the two compounds are administered sufficiently close in time to achieve the intended effect. Typically, if one agent is administered within about the half-life of the first agent, the two agents are considered to be concurrently administered. The active agents may be administered together in a single pharmaceutical composition or separately. Both active agents (i.e., IL-10 and interferon-α) should be present in the patient at sufficient combined levels to be therapeutically effective. The routes of administration and the duration of administration of the IL-10 and interferon-α may be the same or different.

The interferon-α, including pegylated IFN-α, can also be delivered by standard gene therapy techniques, including e.g., direct DNA injection into tissues, the use of recombinant viral vectors, or phospholipid and implantation of transfected cells. See, e.g., Rosenberg, 1992, J including *Clin. Oncol.* 10:180. Or WO 98/35554 (published pegylated IFN-αAug. 20, 1998).

When the pegylated IFN-α administered is a pegylated interferon alfa-2b, the therapeutically effective amount of pegylated interferon alfa-2b administered during the treatment in accordance with the present invention is in the range of about 0.1 to 9.0 micrograms per kilogram of pegylated interferon alfa-2b administered per week, in single or divided doses, preferably once a week (QW) or twice a week(BIW), preferably in the range of about 0.1 to about 9.0 micrograms per kilogram of pegylated interferon alfa-2b administered once a week (QW) or in the range of about 0.05 to about 4.5 micrograms per kilogram of pegylated interferon alfa-2b administered twice a week(BIW), or is in the range of about 0.5 to about 3.0 micrograms per kilogram of pegylated interferon alfa-2b administered per week, preferably in the range of about 0.5 to about 3.0 micrograms per kilogram of pegylated interferon alfa-2b administered once a week (QW) or in the range of about 0.25 to about 1.5 micrograms per kilogram of pegylated interferon alfa-2b administered twice a week, or is in the range of about 0.75 to about 2.0 micrograms per kilogram of pegylated interferon alfa-2b administered per week, most preferably is in the range of about 0.75 to about 2.0 micrograms per kilogram of pegylated interferon alfa-2b administered once a week or about 0.375 to about 1.0 micrograms per kilogram of pegylated interferon alfa-2b administered twice a week.

When the pegylated interferon-α administered is a pegylated interferon alfa-2a, the therapeutically effective amount of pegylated interferon alfa-2a administered during the treatment in accordance with the present invention, including in first and second treatment time periods, is in the range of about 50 micrograms to about 500 micrograms once a week("QW"), preferably about 200 micrograms to about 250 micrograms QW or the effective amount is in the range of about 50 micrograms to about 250 micrograms twice a week, preferably about 100 micrograms to about 125 micrograms twice a week.

Pharmaceutical composition of pegylated interferon alfa-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g. NaCl), preservatives (e.g. thimerosol, cresol or benyl alcohol), and surfactants (e.g. tween or polysorabates) in sterile water for injection. The pegylated interferon alfa-may be stored as lyophilized powders under a refrigeration at 2–8° C. The reconstituted aqueous solutions are stable when stored between 2° and 8° C. and used within 24 hours of reconstitution. See for example U.S. Pat. Nos. 4,492,537; 5,762,923 and 5,766,582. The reconstituted aqueous solutionsmay also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alfa powder in a separate compartment.

In the practice of the invention, IL-10 is administered to a difficult-to-treat patients, exhibiting one of more of the above signs or symptoms in an amount and for a period of time sufficient to eliminate or at least alleviate one or more of the above-mentioned signs or symptoms.

The amount of zidovudine(AZT)-available from Glaxo Wellcome under the EPIVIR tradename—is typically 200 mg, PO, tid or 300 mg, PO, bid. The amount of lamivudine-available from Glaxo Wellcome under the RETROVIR tradename—is typically 150 mg,PO, bid, The amount of ribavirin-available from Schering-Plough Corp under the REBETOL tradename—is about 600 mg/day to about 1200 mg/day, PO, preferably about 800 mg/day to about 1200 mg/day, PO, and most preferably about 1000 mg/day to about 1200 mg/day, PO. The exact amount of zidovudine, lamivudine and ribavirin will be determined by the attending clinician in view of the product information sheet, the age and health of the patient and the severity of the liver disease.

The present invention is more particularly described in the following example which is intended as illustrative only since numerous modifications and variations therein will be apparent to those skilled in the art.

EXAMPLE

Human subjects selected for treatment are anti-HCV antibody positive patients with biopsy documented chronic active hepatitis. Each patient is positive for antibody to hepatitis C virus (anti-HCV) by supplemental assay (Ortho or Abbott) and had previous liver biopsy with features of chronic hepatitis.

Patients are monitored weekly for clinical symptoms, pharmacodynamics including serum IL-10 concentration and antiviral response (ALT normalization, disappearance of hepatitis C RNA (HCV-RNA) by immunoassay and qPCR assay).

To follow the course of HCV replication in subjects in response to drug treatment, HCV RNA is measured in serum samples by, for example, a qPCR assay that uses two sets of primers derived from the NS3 and NS4 non-structural gene regions of the HCV genome. Farci et al., 1991, New Eng. J. Med. 325:98–104. Ulrich et al., 1990*, J Clin. Invest*., 86:1609–1614.

Histological examination of liver biopsy samples is used as a second criteria for evaluation. See, e.g., Knodell et al., 1981*, Hepatology* 1:431–435, or the modified Knodell Score (Ishak et al., J. Hepatol , 1995;22:696–699), or the Metavir scoring system(Bedossa et al., Hepatology, 1996;24:289–293). whose Histological Activity Index "HAI" (portal inflammation, piecemeal or bridging necrosis, lobular injury and fibrosis) provides a scoring method for disease activity. Liver biopsy performed before and at during the last week of IL-10 treatment is conducted to determine the pretreatment severity of liver disease, the histologic response to IL-10 therapy, and the effect of IL-10 on the intrahepatic cellular immune response. Remaining tissue is used to determine $CD8^+$ HCV-specific cell frequency and activity.

In addition to assessing the biochemical, virologic, and histologic response to IL-10 treatment, the impact of the therapy on Th1 and Th2 cytokine profiles and CTL activity is also followed.

Serum samples are obtained at day 0 (pre-treatment), 6 and 12 hours, day 1 (24 hours), day 7, and then weekly for a 3 month treatment period for measurement of HCV RNA and cytokines (TNFα/receptors, IL-1, IL-2, IL-4, IL-10, and IFNγ).

Whole blood is drawn at the same intervals. Peripherial Blood Mononuclear Cells (PBMC) are isolated and analyzed for spontaneous and LPS-induced production of IL-2, TNF, IFN, IL4, and IL-10. PBMC also are used for the evaluation of HCV-specific CTL precursor frequency at the time of liver biopsy to provide peripheral CTL data to correspond with intrahepatic activity.

Each patient's baseline biochemical, virologic and histologic data serves as the control for assessing change. The primary endpoints are ALT, and histological changes between pretreatment and end of treatment liver biopsy. Laboratory research assessments are cytokine levels (serum and PBMC generated) and HCV-specific CTL precursor frequency and activity. HCV RNA levels will also be measured.

The serial analysis of blood before, during and after the completion of therapy provides important information about the time course of changes as well as providing individual patient controls to determine the relative degree of change in each patient and optimum patient dosage. The effectiveness of the therapy of the invention is determined by the extent to which the previously described signs and symptoms of chronic hepatitis, e.g. fibrosis and inflammation, are alleviated and/or eliminated or substantially reduced.

Results of two clinical trails are summarized below. Non-responders are defined as individuals who failed to respond to a previous course of interferon therapy (dose of at least 3 MIU-TIW, for a period of 3 months or longer).

Study I

A trial was conducted of the safety and activity of recombinant human IL-10 in chronic hepatitis C patients.

Study design: Fifteen patients (4 treatment-naive and 11 interferon non-responders) with compensated chronic HCV were administered IL-10 for 28 consecutive days and the effect on ALT and HCV RNA values measured. Patients were randomized to receive recombinant IL-10 at a dose of 4 or 8 μg/kg/day as a single daily subcutaneous injection for 28 days. ALT values and serum HCV RNA (qPCR) were measured at day 0, 1, 3, 8, 15, 22 and 28 during therapy, and at follow-up 2 and 4 weeks after cessation of the 4 week treatment period.

Results:

| | Day 0 | Day 8 | Day 15 | Day 22 | Day 28 | Day 56 |
|---|---|---|---|---|---|---|
| ALT | 116 ± 22 | 88 ± 21 | 65 ± 12 | 69 ± 13 | 69 ± 16 | 96 ± 25 |
| # normal ALT | 0/15 | 8/15 | 9/15 | 8/15 | 8/15 | 3/15 |
| HCV RNA | 4.0 ± 0.8 | 3.0 ± 0.9 | 4.6 ± 1.9 | 3.0 ± 0.8 | 5.3 ± 2.0 | 7.9 ± 3.4 |

Results shown as mean ± SEM.
Treatment was from day 1 to day 28. Follow up values 4 weeks after treatment shown as day 56.
ALT normal range ≦ 45 U/l.
HCV RNA shown as copies/ml × $10^6$.

ALT values normalized in 9 of 15 patients during therapy, but this persisted until end of treatment in only 8 patients. The observed decreases in ALT values occurred equally in both 4 and 8 μg IL-10 dosage groups and was seen in both interferon treatment-naive and non-responder patients. HCV RNA concentrations varied little during therapy. No patients had either an increase or decrease in HCV RNA levels of ≧1.5 log during the study. The drug was well tolerated with no adverse symptoms noted. Platelet counts fell transiently to <100,000/mm$^3$ in 2 patients. No other toxicity was observed. No patient discontinued therapy.

In summary, in chronic hepatitis C, short term therapy with IL-10 caused transient normalization of ALT in 50–60% of patients. This normalization returned to pretreatment levels on cessation of treatment. There was no significant change observed in serum HCV RNA concentrations during or for 4 weeks after therapy. These immunosuppressive-type effects are similar to those observed with ribavirin monotherapy in chronic hepatitis C.

Study II

A trial was conducted of the safety and activity of recombinant human IL-10 in chronic hepatitis C non-responders.

Study design: Ten patients with compensated chronic HCV were administered IL-10 at a dose of either 4 or 8 μg/kg daily for 12 weeks. Efficacy determination was based on ALT, HCV-RNA, and pre- and post-treatment liver histology.

Results: Three month treatment was safe and well tolerated. A decrease in ALT during treatment was observed in approximately 70% of the patients. A significant decrease of HCV-RNA was seen in 1 of the 10 patients. The histologic results showed a significant decrease in hepatic inflammation score (HAI I+II+III) with a mean change from baseline of −1.5 and a significant decrease in fibrosis score (mean change from baseline of −0.96 (standard error +/−0.21).

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for improving liver histology in a patient afflicted with a chronic hepatitis C virus ("HCV") infection comprising administering an effective amount of an interleukin-10 to a patient afflicted with chronic HCV infection who has failed to achieve a sustained virologic response after treatment with any type of anti-HCV therapy comprising interferon-α or pegylated interferon-α alone, or interferon-α or pegylated interferon-α in combination with ribavirin.

2. The method of claim 1 wherein the interleukin-10 is human interleukin-10.

3. The method of claim 1 wherein the interleukin-10 is viral interleukin 10.

4. The method of claim 1 wherein the interleukin-10 is recombinant human interleukin-10.

5. A method for treating hepatic fibrosis in a patient afflicted with a chronic hepatitis C virus ("HCV") infection comprising administering an effective amount of an interleukin-10 to a patient afflicted with chronic HCV infection who has failed to achieve a sustained virologic response after treatment with any type of anti-HCV therapy comprising interferon-α or pegylated interferon-α alone, or interferon-α or pegylated interferon-α in combination with ribavirin.

6. The method of claim 5 wherein the interleukin-10 is human interleukin-10.

7. The method of claim 5 wherein the interleukin-10 is viral interleukin 10.

8. The method of claim 5 wherein the interleukin-10 is recombinant human interleukin-10.

9. A method for modulating the inflammatory response of a patient afflicted with a chronic hepatitis C virus ("HCV") infection comprising administering an effective amount of an interleukin-10 to a patient afflicted with chronic HCV infection who has failed to achieve a sustained virologic response after treatment with any type of anti-HCV therapy comprising interferon-α or pegylated interferon-α alone, or interferon-α or pegylated interferon-α in combination with ribavirin.

10. The method of claim 9 wherein the interleukin-10 is human interleukin-10.

11. The method of claim 9 wherein the interleukin-10 is viral interleukin 10.

12. The method of claim 9 wherein the interleukin-10 is recombinant human interleukin-10.

* * * * *